(12) United States Patent
Cundiff et al.

(10) Patent No.: US 10,533,836 B2
(45) Date of Patent: Jan. 14, 2020

(54) MULTIDIMENSIONAL COHERENT SPECTROSCOPY USING FREQUENCY COMBS

(71) Applicant: THE REGENTS OF THE UNIVERSITY OF MICHIGAN, Ann Arbor, MI (US)

(72) Inventors: Steven T. Cundiff, Ann Arbor, MI (US); Bachana Lomsadze, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 15/705,511

(22) Filed: Sep. 15, 2017

(65) Prior Publication Data

US 2018/0073856 A1 Mar. 15, 2018

Related U.S. Application Data

(60) Provisional application No. 62/394,771, filed on Sep. 15, 2016.

(51) Int. Cl.
| | |
|---|---|
| *G01J 3/45* | (2006.01) |
| *G01B 9/02* | (2006.01) |
| *G01N 21/25* | (2006.01) |
| *H01S 3/13* | (2006.01) |
| *H04B 10/50* | (2013.01) |
| *G01N 21/31* | (2006.01) |

(52) U.S. Cl.
CPC ............ *G01B 9/02008* (2013.01); *G01J 3/45* (2013.01); *G01N 21/255* (2013.01); *G01N 21/31* (2013.01); *H01S 3/13* (2013.01); *H04B 10/506* (2013.01)

(58) Field of Classification Search
CPC .. G01B 9/02008; G01N 21/31; G01N 21/255; H04B 10/506; G01J 3/45; H01S 3/13
See application file for complete search history.

(56) References Cited

U.S. PATENT DOCUMENTS 6,031,612 A * 2/2000 Shirley ............... G01B 11/2531
356/511
8,564,785 B2  10/2013 Newbury et al.
(Continued)

FOREIGN PATENT DOCUMENTS

WO WO 2007045461 A1 * 4/2007 ............... G01J 3/433

OTHER PUBLICATIONS

Znakovskaya et al "Dual Frequency Comb Spectroscopy With a Single Laser", Opt. Lett 39 5471-5474 (2014).
(Continued)

*Primary Examiner* — Hwa Andrew Lee
(74) *Attorney, Agent, or Firm* — Harness, Dickey & Pierce, P.L.C.

(57) ABSTRACT

Dual laser frequency combs can rapidly measure high resolution linear absorption spectra. However, one-dimensional linear techniques cannot distinguish the sources of resonances in a mixture of different analytes, nor separate inhomogeneous and homogeneous broadening. These limitations are overcome by acquiring high resolution multidimensional non-linear coherent spectra with frequency combs.

15 Claims, 11 Drawing Sheets

(56) References Cited

U.S. PATENT DOCUMENTS

| | | | |
|---|---|---|---|
| 8,625,101 B2* | 1/2014 | Giaccari | G01J 3/453 |
| | | | 356/451 |
| 2012/0026507 A1* | 2/2012 | Szwaykowski | G01B 9/02057 |
| | | | 356/495 |
| 2015/0159990 A1 | 6/2015 | Plusquellic et al. | |
| 2015/0325978 A1 | 11/2015 | Fertig et al. | |
| 2015/0380892 A1 | 12/2015 | Fermann et al. | |
| 2018/0292441 A1* | 10/2018 | Koldiaev | G01N 21/8806 |

OTHER PUBLICATIONS

Cundiff et al "Optical Multidimensional Coherent Spectroscopy" Physics Today 66 (7), 44 (2013).

Fuller et al "Experimental Implementations of Two-Dimensional Fourier Transform Electronic Spectroscopy" Annual Review of Physical Chemistry vol. 66 (2015).

Coddington et al, "Coherent Multiheterodyne Spectroscopy Using Stabilized Optical Frequency Combs" Physical Review Letters 100 (1), 013902 (2008).

Newbury, et al, "Sensitivity of Coherent Dual-Comb Spectroscopy", Opt. Express 18 ;(8), 7929-7945 (2010).

Dai et al "Two-dimensional Fourier-transform Spectroscopy of Potassium Vapor" Phys. Rev. A 82 (5), 052503 (2010).

Asplund, et al "Two-Dimensional Infrared Spectroscopy of Peptides by Phase-Controlled Femtosecond Vibrational Photon Echoes", Proc. Nat. Acad. Sci. USA 97, 8219-8224 (2000).

Coddington et al "Dual-Comb Spectroscopy", Optica vol. 3, No. R (2016).

* cited by examiner

MULTIDIMENSIONAL COHERENT SPECTROSCOPY USING FREQUENCY COMBS

CROSS-REFERENCE TO RELATED APPLICATIONS

This application claims the benefit of U.S. Provisional Application No. 62/394,771, filed on Sep. 15, 2016. The entire disclosure of the above application is incorporated herein by reference.

GOVERNMENT CLAUSE

This invention was made with government support under 2016-16041300005, awarded by the Office of the Director of National Intelligence, IARPA. The Government has certain rights in the invention.

FIELD

The present disclosure relates to multidimensional coherent spectroscopy using frequency combs.

BACKGROUND

Optical multi-dimensional coherent spectroscopy (MDCS) is an extremely powerful technique developed over the last two decades for studying structure and ultrafast dynamics. Specifically, MDCS is a non-linear optical technique based on concepts originating in nuclear magnetic resonance (NMR) spectroscopy that enabled the determination of molecular structure. Its empowering features include the capacities to decouple homogeneous and inhomogeneous linewidths, to identify couplings between the excited states, and to track the energy redistribution (in real time) in complex systems. MDCS uses a sequence of (typically three) laser pulses to excite the sample. A multi-dimensional spectrum is then generated by calculating Fourier transforms of the signal with respect to the time delays between pulses and the time period during which the signal is emitted. However, current MDCS implementations have long acquisition times (when implemented with mechanical delay stages) and/or limited spectral resolution (e.g., >10 GHz, limited by spectrometer resolution or the achievable time delays). These attributes limit their applications for studying atomic systems and performing molecular fingerprint ro-vibrational spectroscopy. In addition, MDCS has not been used beyond research laboratories because of the bulky arrangements and complex phase cycling schemes necessary to suppress background linear signals.

This disclosure proposes to overcome these weaknesses of MDCS by leveraging the technique of dual comb spectroscopy (DCS), which has emerged as a revolutionary optical method that enables the rapid acquisition of high resolution, broad absorption spectra.

This section provides background information related to the present disclosure which is not necessarily prior art.

SUMMARY

This section provides a general summary of the disclosure, and is not a comprehensive disclosure of its full scope or all of its features.

A method is presented for multi-dimensional coherent spectroscopy using frequency combs. The method includes: generating a first beam of light, generating a second beam of light and combining the first beam of light with the second beam of light to form an interrogating beam, such that the first beam of light exhibits a frequency comb in the frequency domain, the second beam of light exhibits a frequency comb in the frequency domain, and the frequency comb of the first beam differs from the frequency comb of the second beam. The interrogating beam is directed towards a sample of interest, wherein the interrogating beam is incident upon the sample of interest and intensity of interrogating beam generates a detectable four-wave mixing signal when the interrogating beam interacts with the sample of interest. After the interrogating beam passes through the sample of interest, a reference beam of light is combined with the interrogating beam, where the reference beam is generated from a reference light source that differs from one or more light sources used to generate the first and second beams of light. Lastly, the combined beam is recorded using a photodetector and a two-dimensional spectrum for the sample of interest is determined from the recorded combined beam. The two-dimensional spectrum may be decomposed into individual spectra for constituent elements of a mixture comprising the sample of interest.

In one embodiment, the first beam of light and the second beam of light are generated from a single light source that differs from the reference light source, such that the first beam of light and the second beam of light have same repetition rate but different offset frequencies. In this case, the time delay between incident pulses of the first beam of light and the second beam of light is adjusted using an optical delay line. it is also noted that the reference beam is preferably generated with a different repetition rate than the first beam of light and the second beam of light.

In another embodiment, the first beam of light and the second beam of light are generated from two different light sources, such that the two light sources have different repetition rates.

In another aspect of this disclosure, a system is presented for multi-dimensional coherent spectroscopy using frequency combs. The system includes: a light module, a first beam combiner, a reference light source, a second beam combiner and a signal processor. The light module is configured to generate a first beam of light and a second beam of light, wherein the first beam of light exhibits a frequency comb in the frequency domain, the second beam of light exhibits a frequency comb in the frequency domain, and the frequency comb of the first beam differs from the frequency comb of the second beam. The first beam combiner is configured to receive a first beam of light and a second beam of light, wherein the first beam combiner combines the first beam of light with the second beam of light to form an interrogating beam and directs the interrogating beam towards a sample of interest, such that intensity of interrogating beam generates a detectable four-wave mixing signal when the interrogating beam interacts with the sample of interest. The reference light source is configured to generate a reference beam of light, where the reference light source differs from one or more light sources used to generate the first and second beams of light. The second beam combiner is configured to receive the interrogating beam and the reference beam, wherein the second beam combiner combines the interrogating beam with the reference beam to form a combined beam and directs the combined beam towards a photodetector. The signal processor is interfaced with the photodetector, wherein the signal processor records the combined beam in a non-transitory data store and determines a two-dimensional spectrum for the sample of interest from the recorded combined beam.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3A:
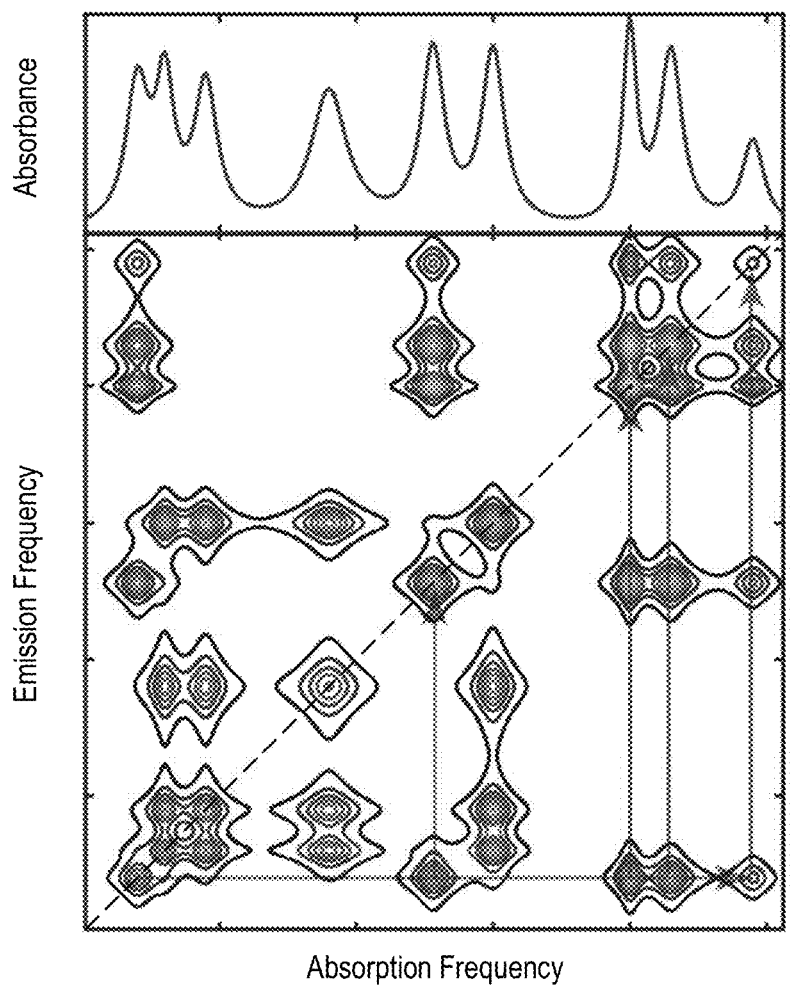
Figure 3B:
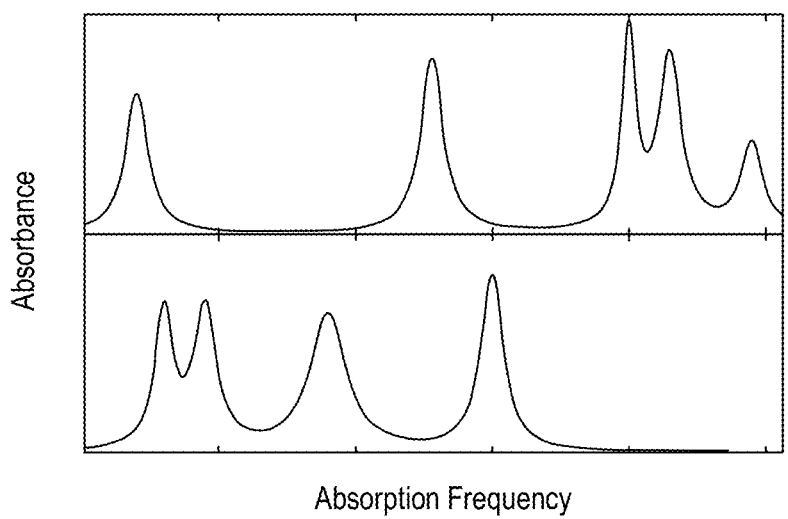
Figure 4:
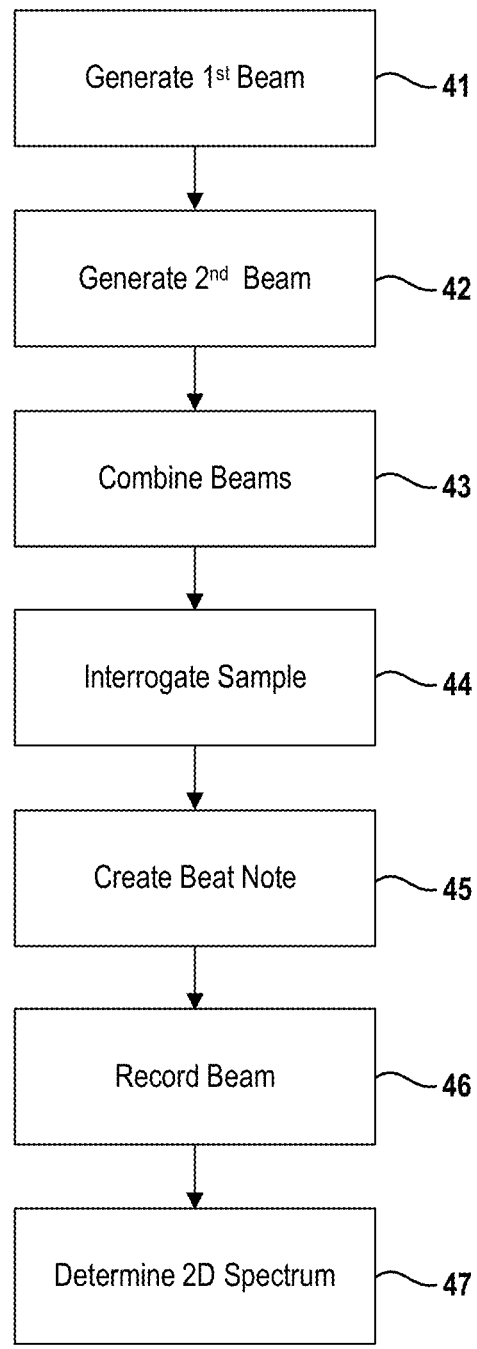
Figure 5:
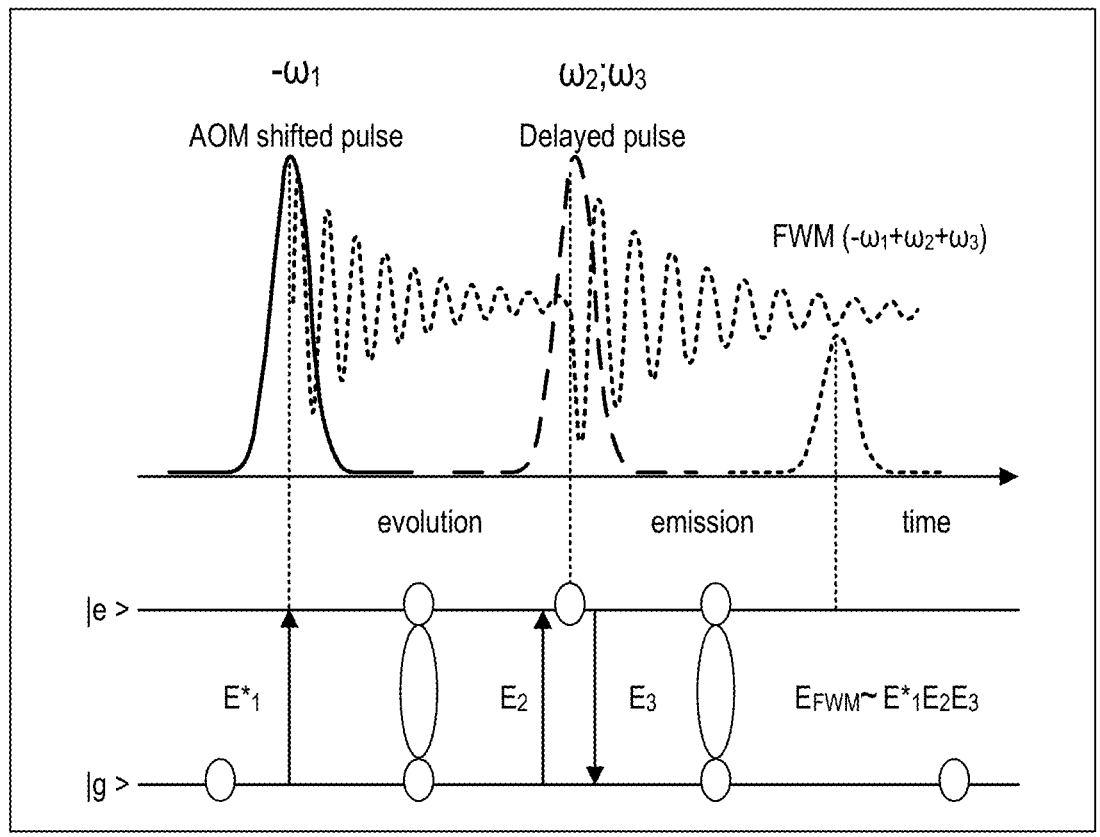
Figure 6A:
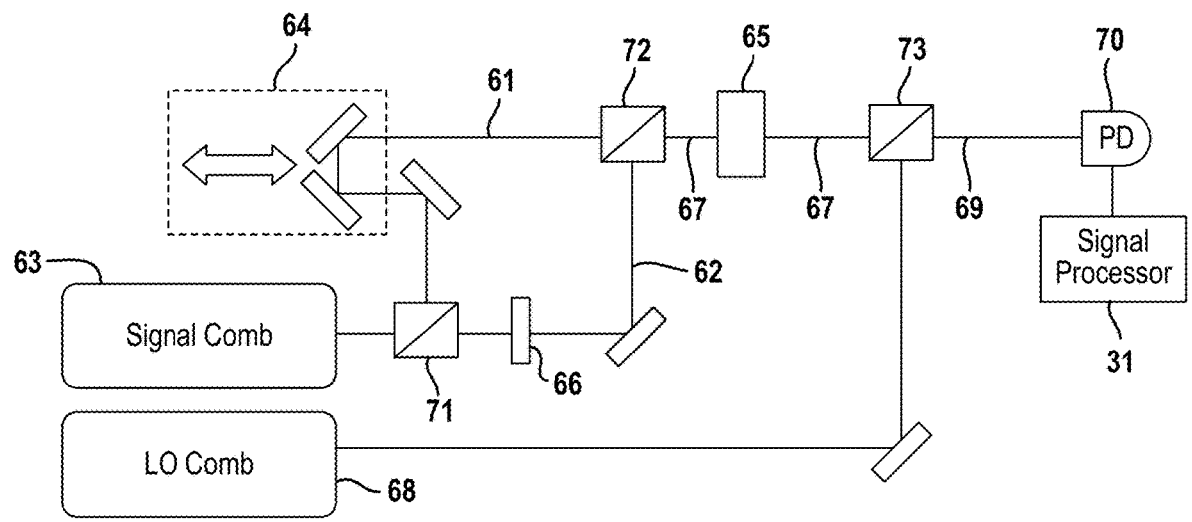
Figure 6B:
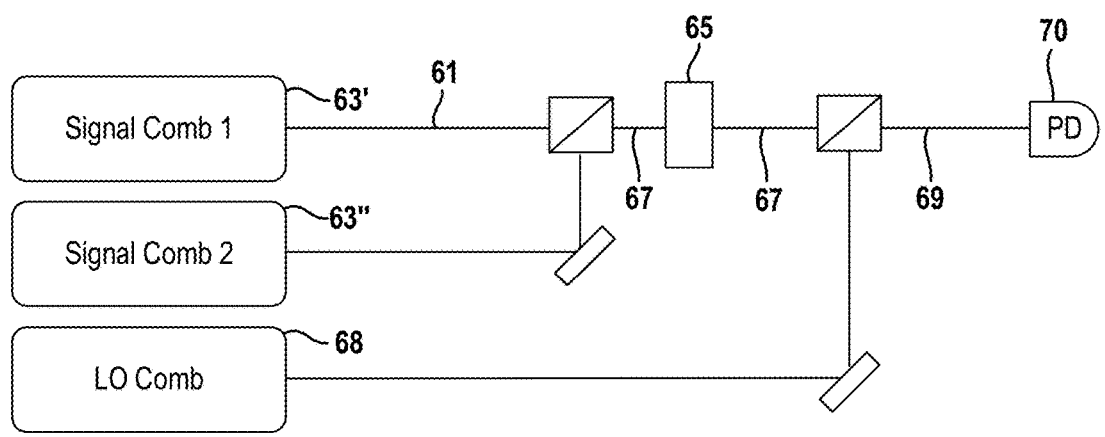
Figure 7:
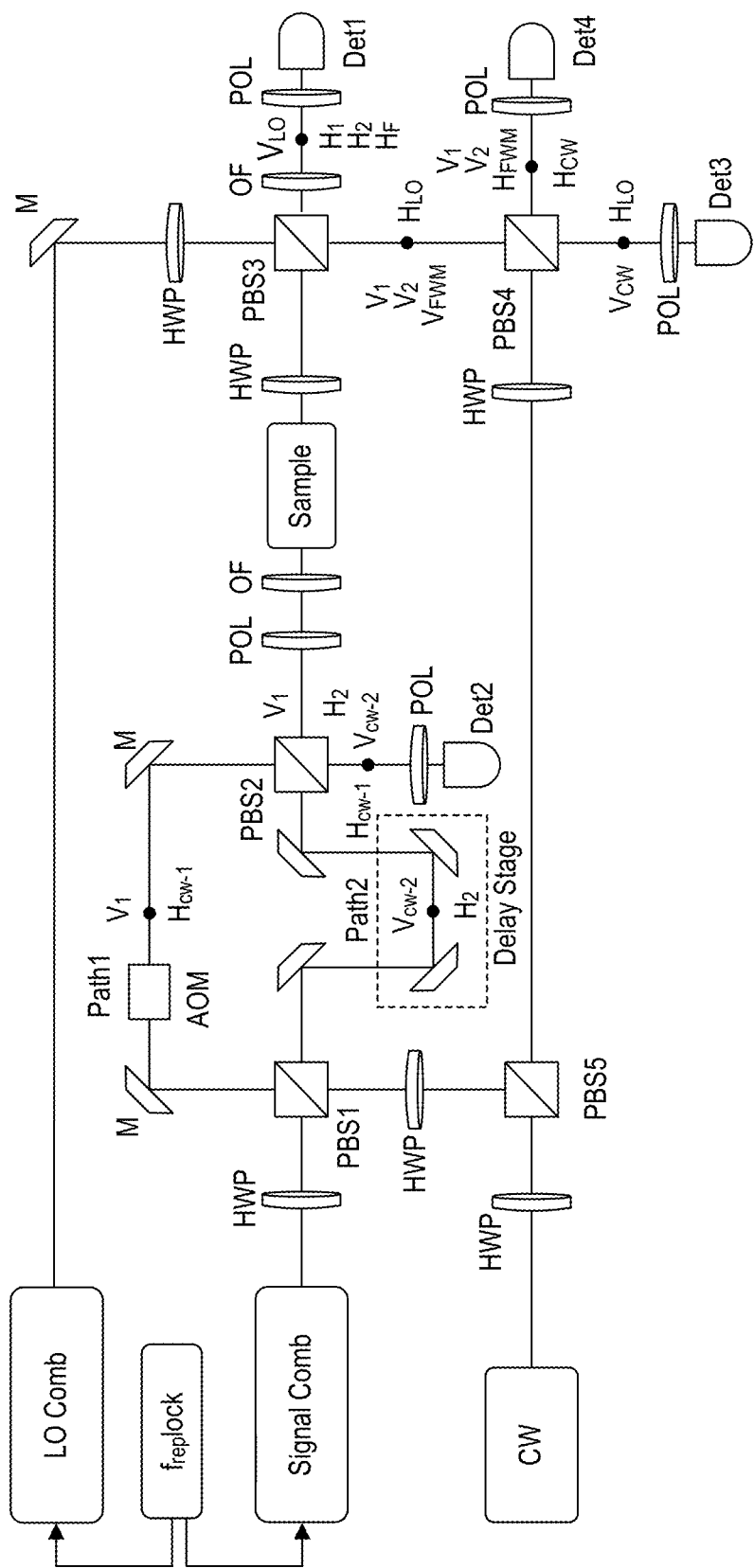
Figure 8:
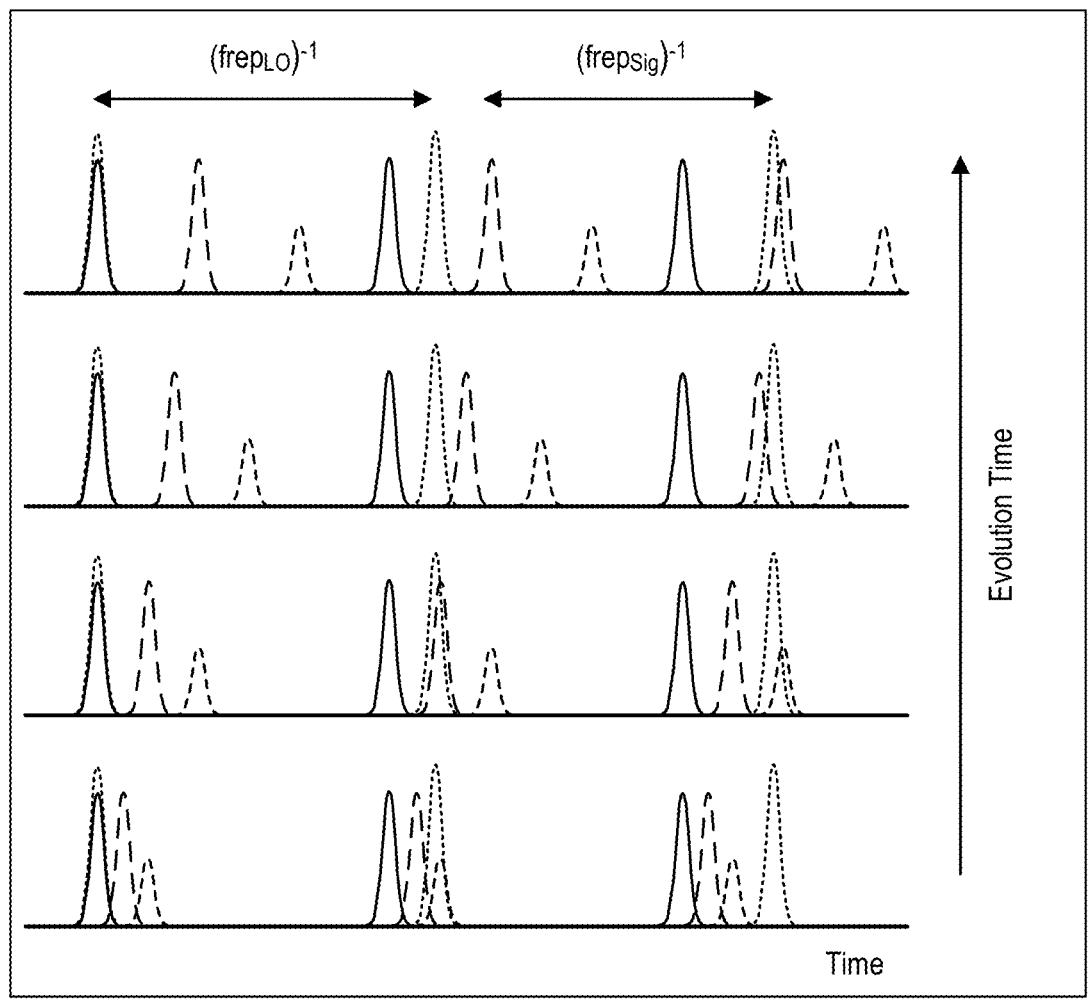
Figure 9:
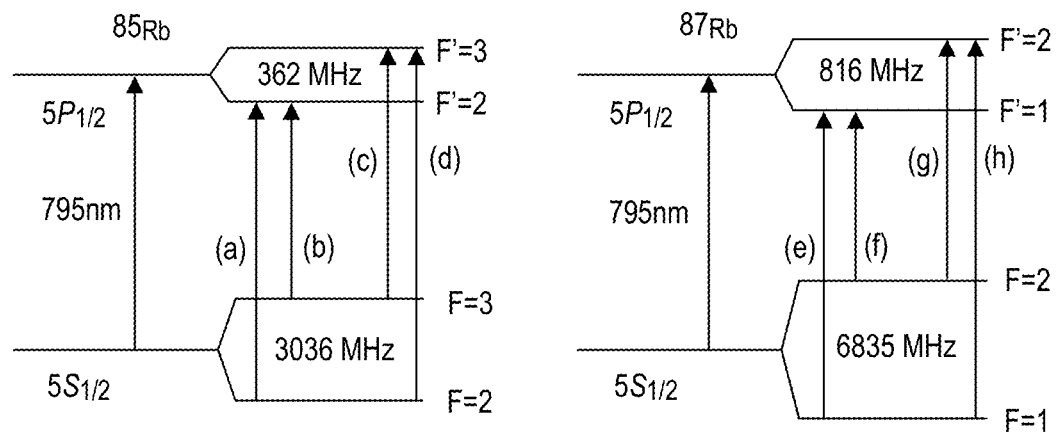
Figure 9:
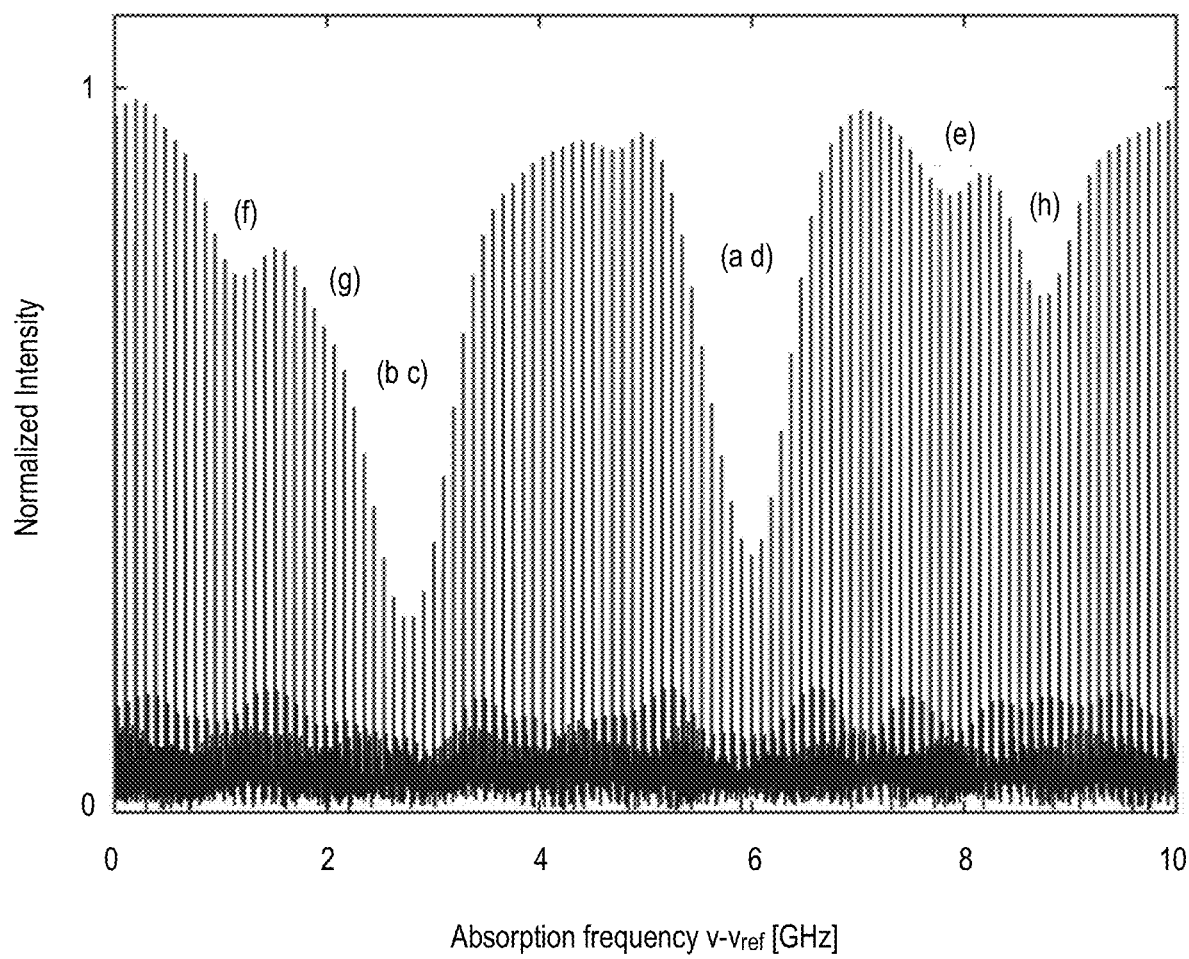
Figure 10A:
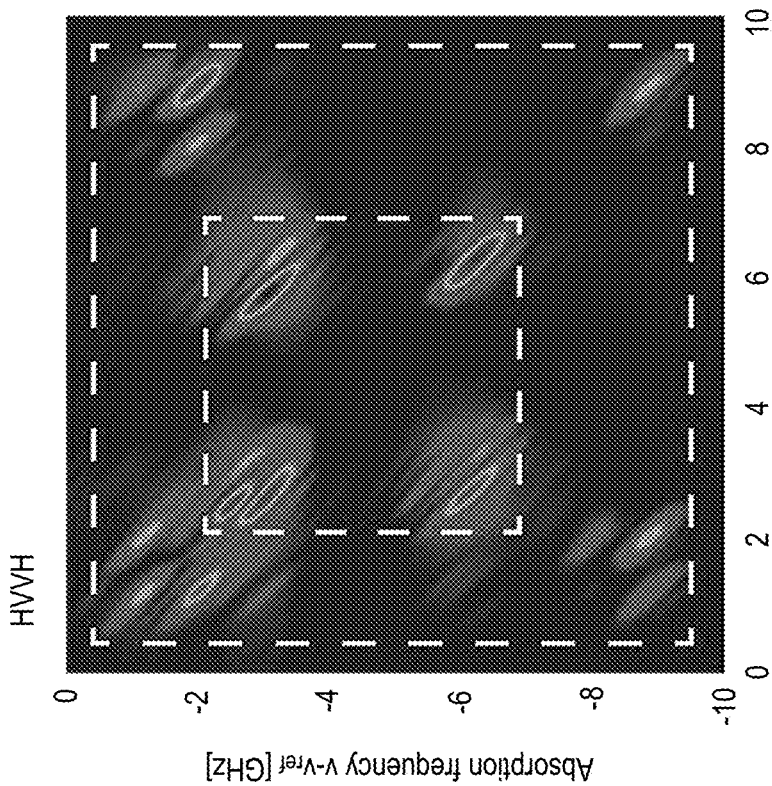
Figure 10B:
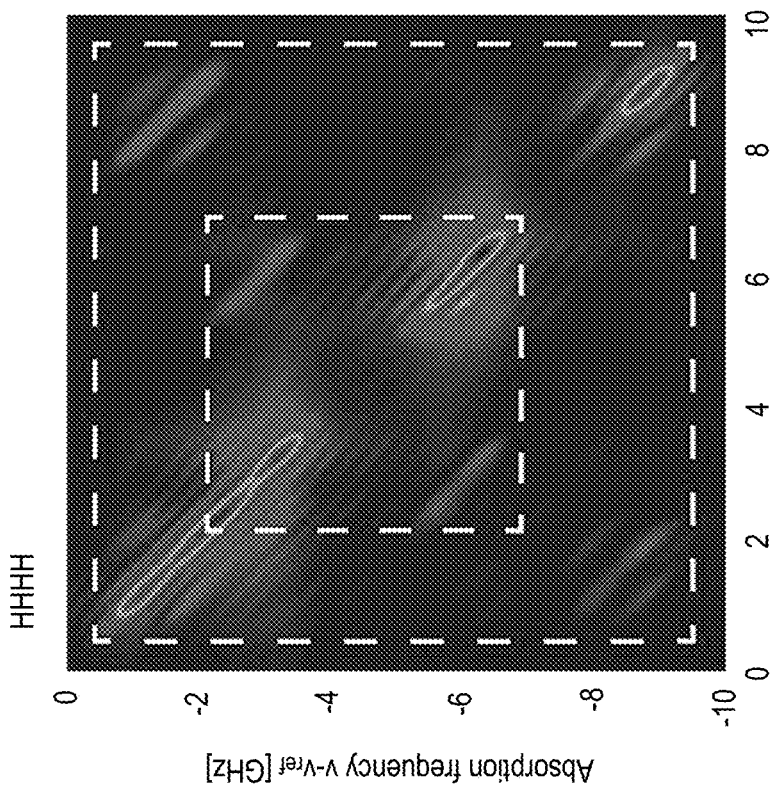
Figure 10D:
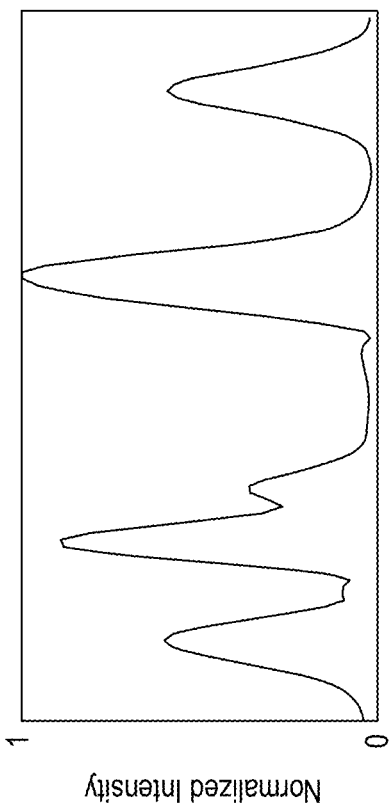
Figure 10C:
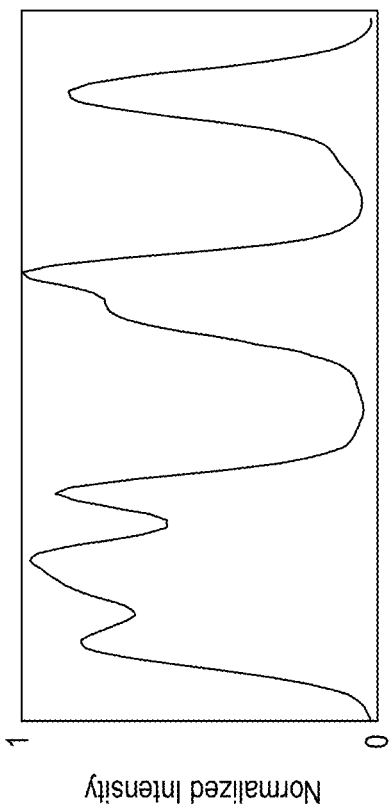
Figure 10F:
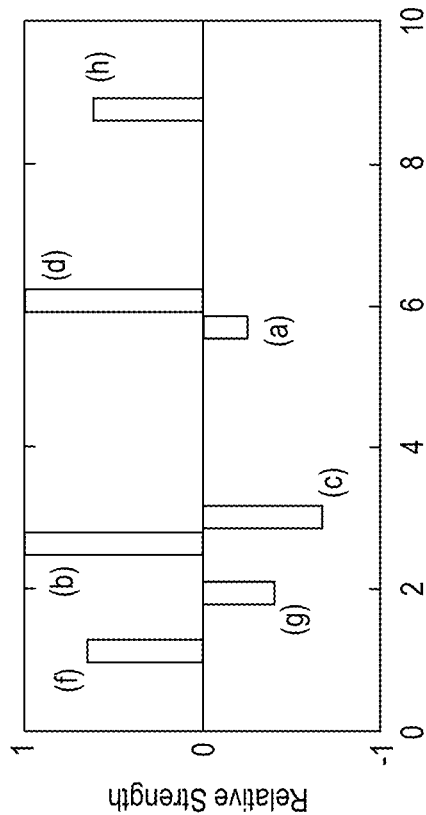
Figure 10E:
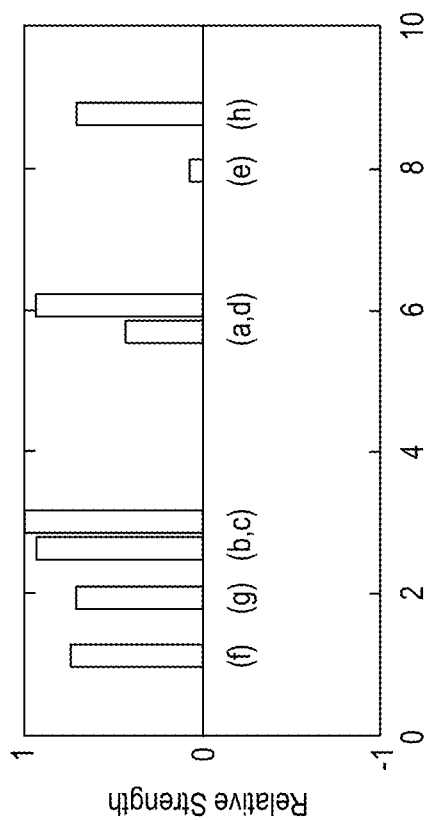

FIGS. 3A-B are diagrams showing how a 2D spectrum can be used to decompose the spectrum of a mixture into individual spectra of the constituents;

FIG. 4 is a flowchart depicting a proposed method for multi-dimensional coherent spectroscopy using frequency combs;

FIG. 5 is a diagram showing the generation scheme of a four-wave-mixing (FWM) signal in the photon echo excitation sequence;

FIG. 6A is diagram of an example system for implementing the proposed method for multi-dimensional coherent spectroscopy;

FIG. 6B is a diagram of another example system for implementing the proposed method for multi-dimensional coherent spectroscopy;

FIG. 7 is a diagram of an experimental setup for demonstrating the proposed concept;

FIG. 8 is a diagram showing the pulses from a reference beam sweeping through the excitation of FWM pulses at different delay times;

FIG. 9 depicts an energy level diagram for rubidium and the measured linear transmission spectrum;

FIGS. 10A and 10B show measured two-dimensional spectra generated by collinearly and cross-linearly polarized excitation pulses, respectively;

FIGS. 10C and 10D show diagonal slices of the spectra in FIGS. 10A and 10B, respectively;

FIGS. 10E and 10F are graphs of the theoretical calculations showing the strength of the FWM signal generated by co-linearly and cross-linearly polarized excitation pulses (where a-h refer to the transitions shown in FIG. 9).

Corresponding reference numerals indicate corresponding parts throughout the several views of the drawings.

DETAILED DESCRIPTION

Example embodiments will now be described more fully with reference to the accompanying drawings.

Optical MDCS is based on concepts originating in multidimensional Fourier transform nuclear magnetic resonance (NMR) spectroscopy. In NMR, the development of multi-dimensional methods enabled the determination molecular structure. Since the underlying concepts are similar in NMR and optical spectroscopy, extending these methods to the optical regime was a logical step. However they require control and measurement of the phases of the electromagnetic waveforms, which is relatively straightforward for the RF signals in NMR, but difficult in optics.

Figure 1:
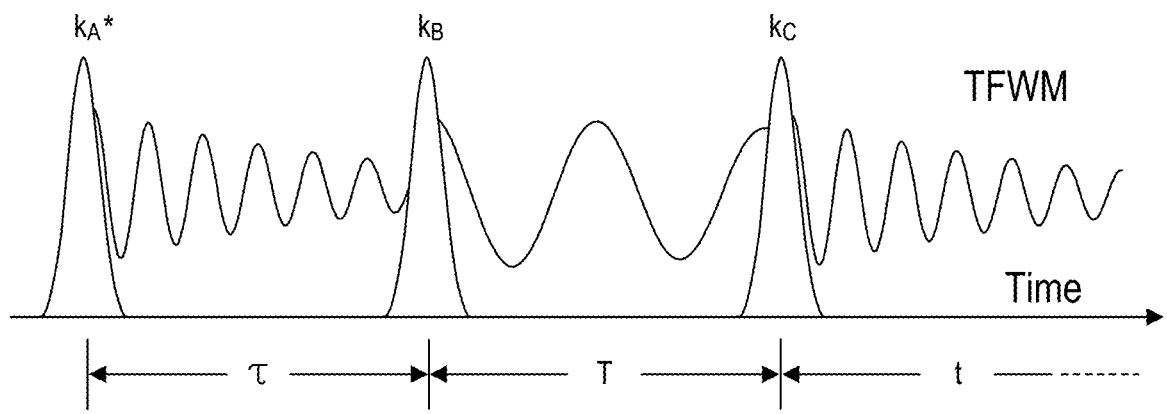
FIG. 1 is a diagram showing a typical pulse sequence used in two-dimensional coherent spectroscopy.

MDCS utilizes a sequence of pulses to excite the sample. The nonlinear interaction of the pulses mediated by the sample results in the emission of a coherent optical signal, known as a transient four-wave-mixing (TFWM) signal. A typical pulse sequence is shown in FIG. 1. The first pulse excites a coherence (quantum mechanically a coherent superposition state) between the ground state and an excited state. The second pulse converts the coherence to an excited state population. The third pulse then converts the population to a third-order coherence that radiates the TFWM signal.

Simply measuring the time-integrated signal intensity as a function of the delay $\tau$ is photon-echo spectroscopy. There are two key enhancements required to perform 2 DCS. First, the phases of the excitation pulses must be stable, and preferably the steps should be exact to a fraction of a wavelength. Second, the electric field, not the intensity, of the signal must be measured as a function of the emission time $\tau$. If both of these are achieved, the emitted signal is coherently measured as a function of both $\tau$ and t and a 2D Fourier transform is taken.

Figure 2:
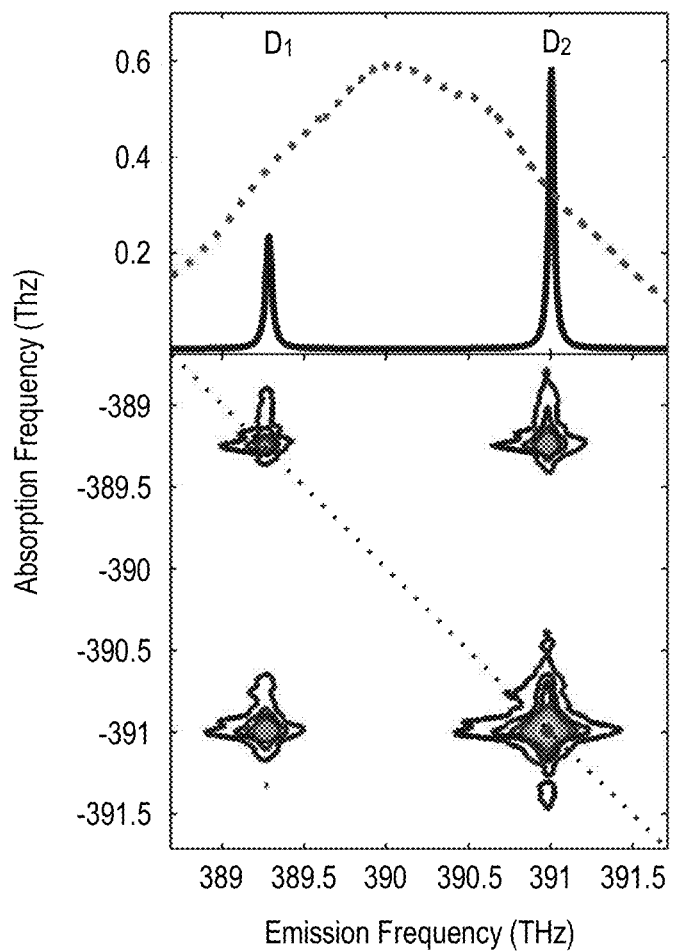
FIG. 2 is a graph illustrating a two-dimensional spectrum of a potassium vapor.

Taking a 2D Fourier transform correlates any resonant signals during the two time periods. If two resonances are correlated, that means that they are coupled to one another. As an example, FIG. 2 shows the experimental 2 DCS of a potassium vapor taken in the laboratory. The vertical axis is obtained by taking the Fourier transform respect to $\tau$, while the horizontal axis corresponds to the Fourier transform with respect to $\tau$. These two frequencies have opposite signs for the 'rephasing' pulse sequence used here and it was chosen to make the emission frequency positive, thus the absorption frequency is negative. The two-dimensional spectra show two peaks on the diagonal, at the frequencies of the $D_1$ and $D_2$ transition. In addition, there are "cross peaks" off the diagonal, i.e., at the absorption frequency of the $D_1$ line and the emission frequency of the $D_2$ line, and vice-versa. These cross-peaks show that the two transitions are coupled, in this case because they share a state. This fact cannot be determined from a linear spectrum, for example, the absorption spectrum shown in the upper panel of FIG. 2, which is also consistent with a sample that is a mixture of two species that each had a single resonance.

The ability of 2 DCS to determine if two resonances are coupled, and thus due to the same species, allows a cluttered spectrum to be decomposed into the individual spectra of the constituent species without any additional information. Being able to decompose spectra in this way could completely solve the problem of spectral clutter in chemical sensing applications of optical/infrared spectroscopy.

FIGS. 3A and 3B show a cartoon spectrum for a sample consisting of a mixture of two substances, each with multiple resonances. In FIG. 3A, the linear spectrum (top) has many resonances. From this spectrum, the number of species cannot be determined. However, the off-diagonal peaks in the 2 DCS indicate which resonances are coupled to another. These can be used to group the resonances and generate spectra for the individual species, without knowledge of the possible species or referring to an atlas of known spectra. The arrows on the 2D spectrum sketch the process of identifying coupled peaks and the decomposed spectra are shown in the lower panel.

Using a 2D spectrum to decompose a cluttered spectrum into the spectra of the constituents is the simplest way to exploit the richness of the 2D spectrum. Rather than analyzing the decomposed one-dimensional spectrum, it is also possible to analyze the full two-dimensional spectra. Often the fingerprint spectra are compared to using a barcode to identify the molecule. By analogy, using the two-dimensional spectrum would be like using QR-codes; clearly a QR-code contains much more information than a barcode.

Given these compelling reasons for using two-dimensional coherent spectroscopy in chemical sensing, one might ask why it has not been developed. The reason is obvious, performing 2 DCS requires complex, phase stable interferometer to generate the pulse sequences, which are challenging enough to use in a laboratory setting, not to mention in the field. The typical acquisition time for a two-dimensional spectrum is 10 minutes to hours due to the mechanical delay lines used to scan the delays. This acquisition time also is not compatible with the needs of chemical sensing. In addition the mechanical delay lines are bulky, even if the path is folded, limiting the ability to make the spectrometers compact. A possible solution to these obstacles can be found in the development of comb-based methods, particularly dual-comb spectroscopy.

Dual comb spectroscopy (DCS) is similar to traditional Fourier Transform Spectroscopy (FTS), wherein the moving mechanical stage, which limits the acquisition speed, is replaced by using two combs with a slightly different repetition rates. This repetition rate difference provides a scanning linear time delay between the signal pulses, which interrogate the sample, and local oscillator (LO) pulses. The interference between the signal and LO combs on a photodetector produces a time-domain signal that can be Fourier-transformed to produce a radio frequency (RF) comb spectrum that directly maps to the optical absorption spectrum of the sample. DCS has been extended into the long wavelength region and used for many practical applications such as remote sensing and LIDAR. However, DCS is a one dimensional optical method and its measured linewidths suffer from inhomogeneous broadening. In addition, DCS shares the drawback of other one dimensional optical methods—an inability to distinguish the sources of different resonances in a sample with multiple analytes.

This disclosure combines multidimensional coherent spectrospocy with comb-based techniques. Specifically, a generalization of dual comb spectroscopy will result in a spectroscopic technique that leverages the advantages of MDCS, namely the ability to decompose cluttered spectra into constituent species while having the characteristics needed for a field-deployable chemical sensing system. An overview of the proposed method is further described in relation to FIG. 4.

As a starting point, two beams of light are generated at steps 41 and 42. Each of the two beams exhibit a frequency comb in the frequency domain. In particular, the frequency comb in the first beam differs (e.g., in repetition rate) from the frequency comb in second beam. In one example, the first beam of light, the second beam of light or both are generated using one or more mode-locking lasers. Additional properties for the two beams are further described below.

The first beam is combined at 43 with the second beam of light to form an interrogating beam. When the interrogating beam interacts with a sample of interest, a four-wave mixing signal is created. The generation scheme of a four-wave-mixing (FWM) signal in the photon echo excitation sequence is illustrated in FIG. 5. The first pulse (AOM shifted pulse shown by the bold line) that is a complex phase conjugated pulse ($E^*_1$) excites a coherence between the ground and an excited state; the second pulse (delayed in time, shown by the bold line) converts this coherence into a population into the excited state and then converts this population into the third-order coherence that radiates a four-wave-mixing signal (shown by the lighter shade line) that is measured.

Intensity of the interrogating beam is designed to generate a detectable four-wave mixing signal when the interrogating beam interacts with the sample of interest. A signal is detectable when its strength allows it to be separated from noise, which are fluctuations due to random processes. The required ratio between the strength of the signal and strength of noise, known as the signal-to-noise ratio (SNR), depends on required confidence that the signal is real and not an artifact of the random nature of the noise.

A sample of interest is interrogated at 44 using the interrogating beam. That is, the interrogating beam is directed towards and incident upon the sample of interest. The sample of interest may be a mixture having two or more constituent elements, such as different molecules, atoms, isotopes, etc. For example, the sample of interest may be a mixture of rubidium atoms having two naturally occurring isotopes. It is readily understood that different types of mixtures and/or samples fall within the scope of this disclosure.

After the interrogating beam passes through the sample of interest, the interrogating beam is combined at 45 with a reference beam of light to create a beat note in the RF domain. The first and second beams may be generated from a single light source or two different light sources as will be described below. In either case, the reference beam is generated from a reference light source that differs from the one or more light sources used to generate the first and second beams of light. At step 46, the combined beam is captured using a photodetector and stored in a non-transitory data store. Lastly, a two-dimensional spectrum for the sample of interest is determined at 47 from the recorded combined beam.

In one example embodiment, the first and second beams 61, 62 are generated from a single light source 63 as seen in FIG. 6A. The light source 63 may be a mode-locking laser. Because the first and second beams 61, 62 are generated from the same light source, the frequency combs exhibited by the two beams have the same repetition rate. Before reaching the sample of interest 65, the light beam output by the laser is split by beam splitter 71 and combined again by beam splitter 72 to form an interrogating beam 67 using conventional optic components, such as beam splitters. In the first beam path, the time delay between incident pulses of the first beam 61 and the second beam 62 can be adjusted using an optical delay line 64. In one example, the optical time delay 64 is implemented by a retroreflector mounted on a delay stage although other implementations are contemplated by this disclosure. In the second beam path, the offset frequency of the frequency comb exhibited by the first beam 61 is shifted, for example using an acousto-optical modulator. Other techniques for shifting the offset frequency of the frequency comb are also contemplated by this disclosure. While the offset frequency differs between the frequency combs of the first beam 61 and the second beam 62 in this example embodiment, it is envisioned that the frequency combs may differ in other ways, such as their repetition rate, their optical spectrum or their polarizations.

After the interrogating beam 67 passes through the sample of interest 65, the interrogating beam 67 is combined by a beam splitter 73 with a reference beam of light to form a combined beam 69. The light beams may be combined using conventional optic components, such as beam splitters. Of note, the reference beam is generated from a second light source 68 which differs from the first light source 63. Likewise, the second light source 63 may be a mode-locked laser. The frequency comb exhibited by the reference beam is preferably generated with a repetition rate different than the first and second beams 61, 62. The combined beam 69 is detected using a photodetector 70.

The photodetector 70 is interfaced with a signal processor. The signal processor in turn records the combined beam in a non-transitory data store for subsequent processing. The signal processor also determines a two-dimensional spectrum for the sample of interest from the recorded combined beam. In addition to the signal, signals characterizing fluctuations in the offset frequencies, repetition rates and path lengths may be recorded and input to the signal processor.

In an exemplary embodiment, the signal processor 31 is implemented as a microcontroller. In other embodiments, the signal processor 31 can be or can include any of a digital signal processor (DSP), microprocessor, microcontroller, or other programmable device which are programmed with software implementing the above described methods. It should be understood that alternatively the signal processor is or includes other logic devices, such as a Field Programmable Gate Array (FPGA), a complex programmable logic device (CPLD), or application specific integrated circuit (ASIC). When it is stated that the signal processor 31 performs a function or is configured to perform a function, it should be understood that signal processor 31 is configured to do so with appropriate logic (such as in software, logic devices, or a combination thereof). It is to be understood that the most relevant components have been discussed in relation to FIG. 6A but that other optic components may be needed to implement the system.

The acquisition speed of the arrangement described above is limited by the use of a mechanical delay stage to generate the delay between the two excitation combs. FIG. 6B depicts another example embodiment for an optical arrangement. In this arrangement, the first beam 61 and the second beam 62 are generated using two distinct light sources. That is, the first beam is generated using a first light source 63' and the second beam is generated using a second light source 63". Because the first and second beams 61, 62 are generated from different light sources, the frequency combs exhibited by the two beams have different repetition rates. Likewise, the reference beam generated by a third light source 68 has a repetition rate that differs from both the first beam 61 and the second beam 62. Except with respect to the differences discussed herein, the optical arrangement is the same as described above in relation to FIG. 6A. Using a third comb to replace the mechanical delay stage will reduce the acquisition time to approximately 10 seconds, a decrease of over an order magnitude. In addition, it will improve the spectral resolution by approximately a factor of three because a longer scan range can be achieved. The net effect is a decrease in the resolution-acquisition time product by close to two orders of magnitude compared to the current system, and over 3 orders of magnitude better than the best non-comb based approach.

An experimental setup is further described in relation to FIG. 7. In this setup, the interrogating beam is generated from a single light source labeled Signal Comb and the reference beam is generated from a second light source labeled LO comb. More specifically, two Kerr-lens mode-locked Ti:Sapphire lasers centered at 800 nm were used. The repetition frequencies for Signal comb and LO comb ($f_{rep\_sig}$=93.567412 MHz and $f_{rep\_LO}$=93.567412 MHz-423.45 Hz) were phase locked to a direct digital synthesizer, but the comb offset frequencies were not actively stabilized. The average output power and pulse duration for signal and LO combs were 300 mW, 12 fs and 200 mW, 10 fs, respectively.

Using a half wave plate (HWP) and a polarizing beam splitter (PBS 1), the output of Signal Comb light source was split into 2 parts. The offset frequency of one part was frequency shifted by 80 MHz using an acousto-optical modulator (AOM) and combined with the other part with a beam splitter PBS 2. The delay between the two pulse trains was adjusted and controlled using a retroreflector mounted on a delay stage. The combined interrogating beam was projected on the same linear polarization state (for HHHH experiment) using a polarizer (POL) and interacted with Rb atoms (loaded in a 0.5 mm thin cell and heated up to 110° C.). The optical spectra for the excitation beams were filtered (using optical bandpass line filter (3 nm full width at half-maximum)) to excite the D1 lines of Rb atoms. Average powers for beams travelling through path 1 and path 2 were 1.0 and 2.0 mW, respectively, and were focused to 5 μm spot on the sample. The four-wave-mixing FWM signals emitted by the sample along with the incident beams were combined with the reference beam from LO comb by beamsplitter PBS 3. Half wave plates were adjusted such that only a small fraction of the light from each beam was sent to another beamsplitter PBS 4 to monitor the optical phase fluctuations; whereas, most of the light was sent to photodetector Det 1 to obtain a RF FWM spectrum at each stage delay.

The electrical signal from the detector contained both the linear and FWM signals. They were spectrally separated in the radio frequency domain without implementing complex phase cycling schemes. The delay between two excitation pulses is varied from 0 to 3.3 ns (limited by the stage length) with 10 ps steps to generate the absorption frequency axis for a 2 dimensional spectrum. FIG. 8 pictorially displays the evolution of the FWM signal in the time domain. Two-dimensional spectra were constructed by calculating Fourier transforms with respect to these two time axis.

FIG. 9 shows the energy level diagram and the measured linear transmission spectrum of the Rb $D_1$ lines. The natural linewidths of the hyperfine split transitions (a-h) were ~6 MHz; however the transmission profile was Doppler broadened (580 MHz at 110° C.) and the hyperfine lines strongly overlapped.

To demonstrate full capability of the proposed method, full two dimensional energy spectra were acquired using co-linearly (HHHH) and cross-linearly (HVVH) polarized excitation pulses as seen in FIGS. 10A and 10B, respectively. Comparison of two spectra in general helps to determine the level structure and study many body effects. The negative values on the absorption axis reflect the negative phase evolution during the evolution period in the photon echo excitation sequence (in FIG. 5 the first pulse corresponds to a complex conjugated pulse $E^*_1$ and hence evolves with a negative frequency).

Both two-dimensional spectra provide rich information compared to the linear transmission spectrum. The diagonal peaks (along the (0,0) to (10, −10) line) correspond to absorption and emission at the same (a-h) resonance frequencies. They are elongated in the diagonal direction due to Doppler broadening. However, along the cross-diagonal direction (for each resonance) the inhomogeneity (Doppler broadening) is removed and the line shapes reflect the homogeneous linewidth. Despite broadening of the intrinsic homogeneous linewidth along the cross-diagonal direction (due to the limitations of the scan range achievable with the mechanical stage), one is able to resolve the hyperfine structure and all possible couplings between the resonances that appear at unique locations. For example, in FIG. 10B the peak near (1.5, −2) GHz corresponds to coupling between two excited states of $^{85}$Rb (F'=1 and F'=2) via the same ground state (F=2); whereas, the peak around (2, −9) GHz shows the coupling of two grounds states of Rb (F=1 and F=2) via the same excited state (F'=2). The same peak analysis can be performed on $^{87}$Rb to determine all possible couplings between the excited states. It is also clear that the two-dimensional spectra do not show the coupling peaks between $^{85}$Rb and $^{87}$Rb resonances, indicating that these sources behave as independent atoms. This information is extremely valuable for chemical sensing applications especially when probing a mixture without prior knowledge of its constituent species. The coupling information allows the decomposition of a cluttered spectrum into the individual spectra of the constituents. For Rb, this decomposition is shown in FIGS. 10A and 10B by the white dashed boxes (inner and outer boxes correspond to the spectra of $^{85}$Rb and $^{87}$Rb respectively) that can be plotted separately.

Some of the diagonal peaks are suppressed in the HVVH spectrum compared to the HHHH case. In FIGS. 10C and 10D, diagonal slices of FIGS. 10A and 10B are plotted, respectively. The slices reveal that peaks at frequencies g, c and a are suppressed and the peak at frequency e is absent for HVVH case. To understand this behavior, calculate the strength of each diagonal FWM signal using Clebsch-Gordan coefficients and all possible double-sided Feynman diagrams for each state (including the magnetic sub-levels) in both cases in the circularly polarized (σ±) light bases. Such calculations show that for the HVVH case, the FWM signals for F to F'=F transitions have the opposite sign compared to the F to F'=F±1 transitions. This sign flip causes partial cancelation of neighboring peaks. The calculations also showed that the signal is zero for the F=1 to F'=1 transition of Rb. For the HHHH case, all of the Feynman diagrams have the same sign that results in addition of neighboring peaks rather than cancelation. In FIGS. 10E and 10F, the results of a theoretical calculation are shown for the strengths of the lines (normalized with natural abundance and using the transmission spectrum), which are in good agreement with the experimental results.

The two-dimensional plots show additional interesting behavior due to the complexity of the level system. The strengths of the off-diagonal peaks are not equal to the geometric mean of the corresponding diagonal peak strengths, as would be expected for a simple 3-level system consisting of a single ground state coupled to two excited states. Indeed, some of the off-diagonal peaks are even weaker than their corresponding diagonal peaks. For instance, the peak at (3, −6.5) GHz in FIG. 10A is much weaker compared to the diagonal peaks at (3, −3) GHz and (6.5, −6.5) GHz that correspond to the F=3 to F'=3 and F=2 to F'=3 transitions in $^{85}$Rb, respectively. This result can be explained in the linear polarization basis (π) by considering the fact that each hyperfine state consists of multiple (degenerate) magnetic sublevels with ($m_F$) quantum number (5 states for F=2 and 7 states for F=F'=3). All sublevels of the F=2 and F=3 states (in π basis) contribute for the diagonal peaks (except $m_F$=0 for the F=3 to F'=3 transitions with zero Clebsch-Gordan coefficient); however only ($m_F$=−2, −1, 1, 2) sub-states of the F=2 and F=3 hyperfine states contribute for the off-diagonal peak. The theoretical calculations show good agreement with the experimental results for this and other off-diagonal peaks.

To obtain a multi-dimensional spectrum with comb resolution the relative phase fluctuations between two lasers due to the lasers' optical frequency and path fluctuations can be monitored as seen in FIG. 7. A continuous wave (CW) laser is used to track the phase fluctuations. CW laser, tuned near 794 nm, was split into two parts using a HWP and PBS 5. One part was used to measure the optical phase fluctuations of LO comb and signal comb (caused by the offset, residual repetition frequency and path length fluctuations) on photodetectors Det 3 and Det 4, respectively. The second part was used to track the path fluctuations between path 1 and path 2 on photodetector Det 2. CW laser also served as an optical marker to frequency remap from RF to optical domain and as a reference for the phase evolution of the FWM signal during the evolution period (moving the mechanical stage). The absolute frequency of the CW laser was measured using a spectrometer.

The electrical signals from photodetectors Det 2, Det 3 and Det 4 were used to generate the correction signal. This process was performed digitally where the phase correction was performed using analog electronics. In this experiment, the signals were first combined using analog power splitters/combiners and digitized using a fast (250 MHz sampling rate) digitizer. Det 2, Det 3, and Det 4 contributions were then spectrally separated using Matlab software. Det 1 signal was filtered using a RF bandpass filter to isolate the FWM RF signal from the linear signals, amplified, and digitized on the second channel of the same digitizer. The phase correction of Det 1 signal was performed by multiplying the digitized time domain waveforms according to the scheme shown in FIG. 10. In is also envisioned that the phase correction can be performed using Field Programmable Gate Arrays (FPGA).

In sum, it has been demonstrated that multi-dimensional coherent spectroscopy using frequency combs has much higher spectral resolution than traditional 2-dimensional spectroscopy techniques. This proposed technique resolved Doppler broadened spectral features (at 110° C.) without implementing the complex laser cooling apparatus, applicable only for a few systems. It is also noted that this approach provides fast acquisition speed in addition to high resolution, which is crucial for remote sensing applications.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for multi-dimensional coherent spectroscopy using frequency combs, comprising:
   generating a first beam having a frequency comb in the frequency domain, where the first beam is generated by a first light source;
   generating a second beam having a frequency comb in the frequency domain, where the second beam is generated by a second light source and the second beam of light has a different repetition rate than the first beam of light;
   combining the first beam of light with the second beam of light to form an interrogating beam;
   directing the interrogating beam towards a sample of interest, wherein the interrogating beam is incident upon the sample of interest and intensity of interrogating beam generates a detectable four-wave mixing signal when the interrogating beam interacts with the sample of interest;

combining a reference beam of light with the interrogating beam after the interrogating beam passes through the sample of interest, where the reference beam is generated from a reference light source that differs from the first light source and the second light source;
recording the combined beam using a photodetector; and
determining a two-dimensional spectrum for the sample of interest from the recorded combined beam.

2. The method of claim 1 further comprises decomposing the two-dimensional spectrum into individual spectra for constituent elements of a mixture comprising the sample of interest.

3. The method of claim 1 further comprises generating at least one of the first beam of light or the second beam of light using a mode-locking laser.

4. The method of claim 1 wherein determining the two-dimensional spectrum includes segmenting the recorded combined beam into discrete time intervals.

5. The method of claim 1 further comprises determining the two-dimensional spectrum by Fourier transforming the recorded combined beam.

6. The method of claim 1 wherein the reference beam is generated with a different repetition rate than the first beam of light and the second beam of light.

7. The method of claim 1 further comprises recording signal characteristics for the combined beam, including offset frequency, repetition rates and path lengths.

8. A system for multi-dimensional coherent spectroscopy using frequency combs, comprising:
a first light source configured to generate a first beam of light having a frequency comb in the frequency domain;
a second light source configured to generate a second beam of light having a frequency comb in the frequency domain, where the second beam of light has a different repetition rate than the first beam of light;
a first beam combiner configured to receive the first beam of light and the second beam of light, wherein the first beam combiner combines the first beam of light with the second beam of light to form an interrogating beam and directs the interrogating beam towards a sample of interest, such that intensity of interrogating beam generates a detectable four-wave mixing signal when the interrogating beam interacts with the sample of interest;
a reference light source configured to generate a reference beam of light, where the reference light source differs from the first light source and the second light source;
a second beam combiner configured to receive the interrogating beam and the reference beam, wherein the second beam combiner combines the interrogating beam with the reference beam to form a combined beam and directs the combined beam towards a photodetector; and
a signal processor interfaced with the photodetector, wherein the signal processor records the combined beam in a non-transitory data store and determines a two-dimensional spectrum for the sample of interest from the recorded combined beam.

9. The system of claim 8 wherein the sample of interest is a mixture of two or more constituent elements and the signal processor decomposes the two-dimensional spectrum into individual spectra, such that each spectra corresponds to one of the constituent elements of the mixture.

10. A method for multi-dimensional coherent spectroscopy using frequency combs, comprising:
generating a first beam of light, such that the first beam of light exhibits a frequency comb in the frequency domain;
generating a second beam of light, such that the second beam of light exhibits a frequency comb in the frequency domain, where the frequency comb of the first beam differs from the frequency comb of the second beam;
combining the first beam of light with the second beam of light to form an interrogating beam;
directing the interrogating beam towards a sample of interest, wherein the interrogating beam is incident upon the sample of interest and intensity of interrogating beam generates a detectable four-wave mixing signal when the interrogating beam interacts with the sample of interest;
combining a reference beam of light with the interrogating beam after the interrogating beam passes through the sample of interest, where the reference beam is generated from a reference light source that differs from one or more light sources used to generate the first and second beams of light;
recording the combined beam using a photodetector;
separating the four-wave mixing signal in RF domain using a RF bandpass filter; and
determining a two-dimensional spectrum for the sample of interest from the recorded combined beam.

11. The method of claim 10 further comprises
generating the first beam of light and the second beam of light from a single light source that differs from the reference light source, such that the first beam of light and the second beam of light have same repetition rate but different offset frequencies; and
adjusting time delay between incident pulses of the first beam of light and the second beam of light using an optical delay line.

12. The method of claim 11 wherein the reference beam is generated with a different repetition rate than the first beam of light and the second beam of light.

13. The method of claim 10 further comprises
generating the first beam of light using a first light source; and
generating the second beam of light using a second light source, where the second beam of light has a different repetition rate than the first beam of light and the reference beam is generated with a different repetition rate than the first beam of light and the second beam of light.

14. The method of claim 10 wherein determining the two-dimensional spectrum includes segmenting the recorded combined beam into discrete time intervals.

15. The method of claim 10 further comprises determining the two-dimensional spectrum by Fourier transforming the recorded combined beam.

* * * * *